US011255756B2

(12) United States Patent
Saito et al.

(10) Patent No.: US 11,255,756 B2
(45) Date of Patent: Feb. 22, 2022

(54) TESTING VESSEL AND TESTING METHOD EMPLOYING SAME

(71) Applicant: SEKISUI MEDICAL CO., LTD., Tokyo (JP)

(72) Inventors: Kazunori Saito, Tokyo (JP); Hiroyuki Oono, Tokyo (JP); Kimiyoshi Nishitani, Tokyo (JP); Motoki Morita, Tokyo (JP); Shinji Matsuura, Kobe (JP); Hiroshi Yashiro, Kasama (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 669 days.

(21) Appl. No.: 16/075,074

(22) PCT Filed: Mar. 13, 2017

(86) PCT No.: PCT/JP2017/009986
  § 371 (c)(1),
  (2) Date: Aug. 2, 2018

(87) PCT Pub. No.: WO2017/159616
  PCT Pub. Date: Sep. 21, 2017

(65) Prior Publication Data
  US 2019/0017903 A1   Jan. 17, 2019

(30) Foreign Application Priority Data

Mar. 15, 2016  (JP) .............................. JP2016-051017
Nov. 7, 2016   (JP) .............................. JP2016-217270

(51) Int. Cl.
  *G01N 21/00*   (2006.01)
  *G01N 30/96*   (2006.01)
  (Continued)

(52) U.S. Cl.
  CPC .............. *G01N 1/04* (2013.01); *B01L 3/5029* (2013.01); *B01L 3/5082* (2013.01); *G01N 1/10* (2013.01);
  (Continued)

(58) Field of Classification Search
  CPC ........... G01N 30/00; G01N 2030/0075; G01N 2030/009; G01N 2030/027
  (Continued)

(56) References Cited

U.S. PATENT DOCUMENTS 4,396,024 A    8/1983  Sarstedt
4,859,610 A *  8/1989  Maggio .............. A61B 10/0038
                                                436/518
(Continued)

FOREIGN PATENT DOCUMENTS

JP    3-53876 A    3/1991
JP    3000661 U   8/1994
(Continued)

OTHER PUBLICATIONS

Japanese Notice of Reasons for Refusal dated Jun. 17, 2020, for Japanese Application No. 2017-112693, with an English translation.
(Continued)

*Primary Examiner* — Monzer R Chorbaji
(74) *Attorney, Agent, or Firm* — Birch, Stewart, Kolasch & Birch, LLP

(57) ABSTRACT

A testing vessel 1 includes a flexible vessel body 10 having a bottom and a hollow shape; and a partition 11 axially extending in the vessel body 10 and dividing an analyte extract containable space 50 in the vessel body 10 into two or more compartments. The testing vessel 1 enables two or more items to be readily tested with two or more test pieces.

12 Claims, 16 Drawing Sheets

(51) Int. Cl.
*G01N 33/53* (2006.01)
*G01N 33/72* (2006.01)
*G01N 1/04* (2006.01)
*G01N 1/10* (2006.01)
*G01N 33/543* (2006.01)
*G01N 33/48* (2006.01)
*B01L 3/00* (2006.01)
*G01N 1/28* (2006.01)

(52) U.S. Cl.
CPC .............. *G01N 1/28* (2013.01); *G01N 33/48* (2013.01); *G01N 33/543* (2013.01)

(58) Field of Classification Search
USPC .................. 422/58, 61, 69, 408; 435/7, 296; 436/66, 518, 531
See application file for complete search history.

(56) References Cited

U.S. PATENT DOCUMENTS

| | | | |
|---|---|---|---|
| 4,865,813 A | 9/1989 | Leon | |
| 5,120,503 A * | 6/1992 | Hinckley | G01N 33/5302 422/527 |
| 9,414,813 B2 | 8/2016 | Engel et al. | |
| 9,462,998 B2 | 10/2016 | Engel et al. | |
| 2009/0024055 A1 | 1/2009 | Nguyen et al. | |
| 2012/0094303 A1* | 4/2012 | Engel | G01N 33/558 435/7.1 |
| 2013/0022517 A1 | 1/2013 | Engel et al. | |
| 2015/0173724 A1 | 6/2015 | Engel et al. | |
| 2018/0008240 A1 | 1/2018 | Engel et al. | |

FOREIGN PATENT DOCUMENTS

| | | | |
|---|---|---|---|
| JP | 7-34935 | U | 6/1995 |
| JP | 8-52366 | A | 2/1996 |
| JP | 2001-116739 | A | 4/2001 |
| JP | 2005-189034 | A | 7/2005 |
| JP | 2009-14365 | A | 1/2009 |
| JP | 2009-216651 | A | 9/2009 |
| JP | 2010-38640 | A | 2/2010 |
| JP | 2012-132897 | A | 7/2012 |
| WO | WO 2012/000734 | A1 | 1/2012 |

OTHER PUBLICATIONS

International Search Report (PCT/ISA/210) dated May 9, 2017, issued in PCT/JP2017/009986.

Extended European Search Report, dated Aug. 22, 2019, for European Application 17766616.1.

Office Action dated Sep. 30, 2020, in Chinese Patent Application No. 201780015670.2.

International Preliminary Report on Patentability and English translation of the Written Opinion of the International Searching Authority (Forms PCT/IB/338, PCT/IB/373 and PCT/ISA/237) for International Application No. PCT/JP2017/009986, dated Sep. 27, 2018.

Chinese Office Action (including an English translation thereof) issued in the corresponding Chinese Patent Application No. 201780015670.2 dated May 26, 2021.

Chinese Office Action (including an English translation thereof) issued in the corresponding Chinese Patent Application No. 201780015670.2 dated Oct. 15, 2021.

* cited by examiner

FIG.6A
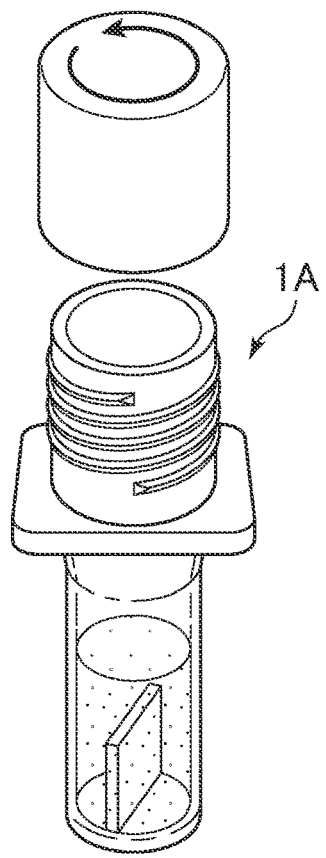
FIG.6B
FIG.6C
FIG.6D
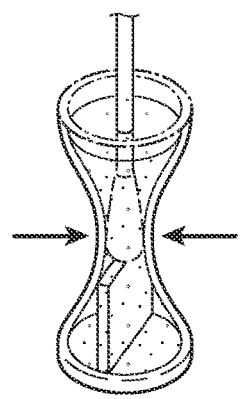
FIG.6E
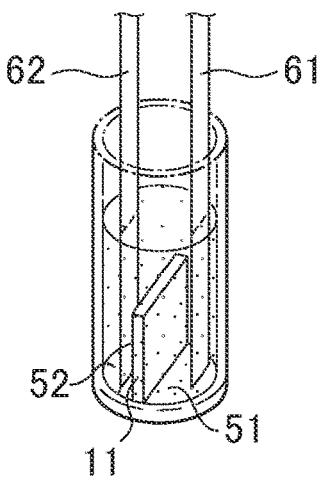

FIG.14F1

FIG.15F2
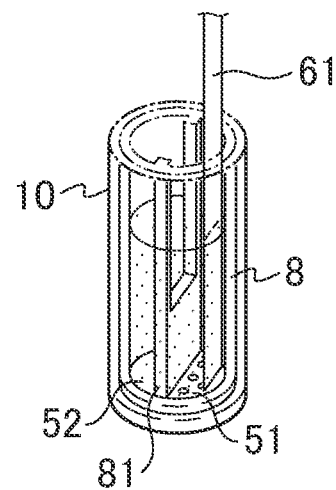
FIG.15G
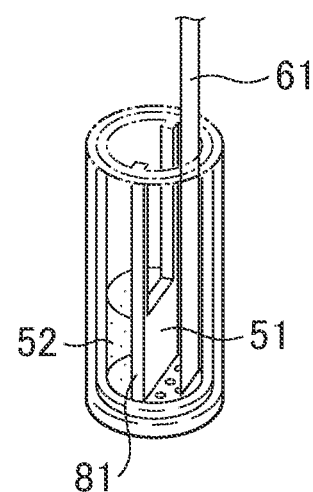
FIG.15H
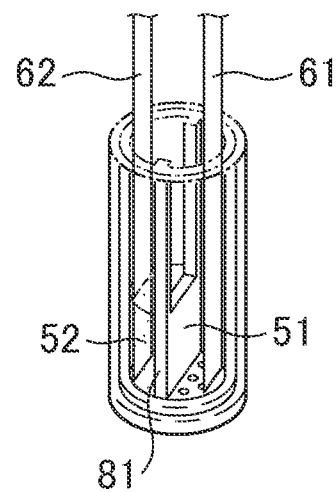

TESTING VESSEL AND TESTING METHOD EMPLOYING SAME

TECHNICAL FIELD

The present invention relates to a testing vessel and a testing method using the vessel, more specifically to a testing vessel facilitating tests for two or more items and a testing method using the vessel.

BACKGROUND ART

Recently, simple test reagents and kits have been developed for performing tests of, for example, the infection with pathogens, such as viruses and bacteria, and of pregnancy, in a short time. Many of such simple test reagents do not require a special facility, are readily operated, and are inexpensive. Unlike other test reagents, the simple test reagents for pathogenic infection have been widely used not only in large hospitals and medical test centers, but also in general hospitals and clinics because patients initially visit these medical institutions in many cases. Thus, if the infection is determined in-situ for the analyte collected from a patient, medical treatment can be made in the early stage. The simple test reagents are increasingly important in health care.

Methods currently adopted in simple test reagents include the assays using membranes, in particular, nitrocellulose membranes for antigen-antibody reaction. The assays are broadly classified into a flow-through assay and a lateral flow assay. Whereas the former causes solutions including target substances to pass through a membrane in the vertical direction, the latter in the horizontal direction. Some lateral flow assays use dipsticks. These assays are common in the formation of a complex consisting of a target substance, an entrapping substance to be bound specific to the target substance, and a marker to be bound specific to the target substance on a solid phase to detect or quantify the marker and thus to detect or quantify the target substance.

A simple membrane assay with an assay device including a membrane having a bound substance for entrapping the target substance collects a portion of a site expected to contain a target substance, causes the target substance to suspend in, for example, a buffer solution, and thereby prepares a sample for the membrane assay. For example, a liquid analyte to be used for the test of, for example, influenza, is collected from the nasal cavity and pharynx of a patient with an analyte collecting tool, such as a swab, and is suspended in a buffer solution.

To release the target substance absorbed in the pledget of the swab therefrom, the pledget is immersed in the analyte extract in an analyte extracting vessel such that the target substance spontaneously elutes, or the pledget undergoes external force such that the target substance is forcibly released (see, for example, Patent Literature 1).

CITATION LIST

Patent Literature

[PLT 1]
Unexamined Utility Model Application Publication No. 3000661

SUMMARY OF INVENTION

Technical Problem

When two or more test pieces are simultaneously immersed in an analyte extract in a traditional testing vessel, some of the test pieces cannot sufficiently absorb the analyte extract and thus may reject exact examination, due to differences in position of immersion and absorption rate between test pieces. If a first test piece is immersed in the testing vessel followed by immersion of a second test piece for another test item, the first test piece completely absorbs the analyte extract, the other item with the second test piece cannot be tested.

Thus, a requirement for testing vessels is to facilitate the tests for two or more items with two or more test pieces.

Solution to Problem (1) A testing vessel including: a flexible vessel body having a bottom and a hollow shape; and a partition axially extending in the vessel body, the partition dividing an analyte extract containable space in the vessel body into two or more compartments.

(2) The testing vessel according to (1), wherein the partition is integrated with the vessel body and extends from the bottom of the vessel body.

(3) The testing vessel according to (1) or (2), wherein the analyte extract containable space in the vessel body is divided into three or more compartments.

(4) The testing vessel according to anyone of (1) to (3), wherein the partition is detachably mounted to the interior of the vessel body with a locking member.

(5) The testing vessel according to any one of (1) to (4), wherein the partition is a hollow pillar partition extending from the bottom of the vessel body.

(6) A test kit including: the testing vessel according to any one of (1) to (5), the testing vessel containable an analyte extract; and a test piece.

(7) A testing method including: impregnating a swab containing an analyte with an analyte extract in a flexible testing vessel, the vessel having an internal space divided into two or more compartments in the axial direction; squeezing the analyte from the swab by deforming the testing vessel with external force; immersing a first test piece into a first compartment of the testing vessel.

(8) The testing method according to (7), further including immersing a second test piece into a second compartment of the testing vessel.

(9) The testing method according to (8), wherein the second test piece is immersed substantially simultaneously with or after immersing the first test piece.

(10) A testing vessel including: a flexible vessel body having a bottom and a hollow shape; and an adapter detachably mounted to the interior of the vessel body, the adapter having a bottom and a hollow shape; wherein the adapter comprises a partition extending from the bottom of the adapter to its opening, the partition dividing an analyte extract containable space in the adapter into two or more compartments.

(11) The testing vessel according to (10), wherein the adapter has a through hole defined in a portion thereof.

(12) The testing vessel according to (10), wherein the adapter has a through hole in at least one of bottom segments of the compartments.

(13) The testing vessel according to any one of (10) to (12), wherein the adapter includes guides extending from the boundary of compartments in the adapter to its opening.

(14) The testing vessel according to (13), wherein the guides each have an upper end located above the edge of the opening of the vessel body.

(15) The testing vessel according to (14), wherein the guides each includes a collar protruding from the upper end of the guide at the opening of the adapter to the exterior of the testing vessel.

(16) The testing vessel according to any one of (10) to (15), wherein the adapter includes a baffle plate disposed along the boundary between the bottom segments of the compartments on the lower face of the adapter so as to be in contact with the upper face of the vessel body, the baffle plate blocking the flow of a solution between the compartments.

(17) The testing vessel according to any one of (10) to (16), wherein the adapter body has an analyte extract containable space divided into three or more compartments.

(18) The testing vessel according to any one of (10) to (17), wherein the outer radius of the adapter is equal or larger than the inner radius of the vessel body.

(19) A test kit including: a testing vessel according to any one of (10) to (18), the vessel containable an analyte extract; and a test piece.

(20) A testing method including: impregnating a swab containing an analyte with an analyte extract in a flexible vessel body, the vessel body having a bottom and a hollow shape; squeezing the analyte from the swab by deforming the testing vessel with external force; inserting an adapter into the vessel body, the adapter having a bottom and a hollow shape, the adapter comprising a partition for dividing an analyte extract containable space in the adapter into two or more compartments, the partition extending from the bottom of the adapter to its opening, at least one of the compartments having a through hole defined in the bottom; and immersing a first test piece into a first compartment of the compartments.

(21) The testing method according to (20), further including immersing a second test piece into a second compartment of the compartments.

(22) The testing method according to (21), wherein the second test piece is immersed substantially simultaneously with or after immersing the first test piece.

Advantageous Effect of Problem

The present invention provides a testing vessel that enables two or more items to be readily tested with two or more test pieces.

BRIEF DESCRIPTION OF DRAWING

FIGS. 6A to 6E illustrate a process flow of a testing method 1A according to an embodiment.

FIGS. 14A to 14F1 illustrate a process flow of a testing method 1B according to an embodiment.

FIGS. 15F2 to 15H illustrate a process flow of a testing method 2B according to an embodiment.

DESCRIPTION OF EMBODIMENTS

Figure 1A:
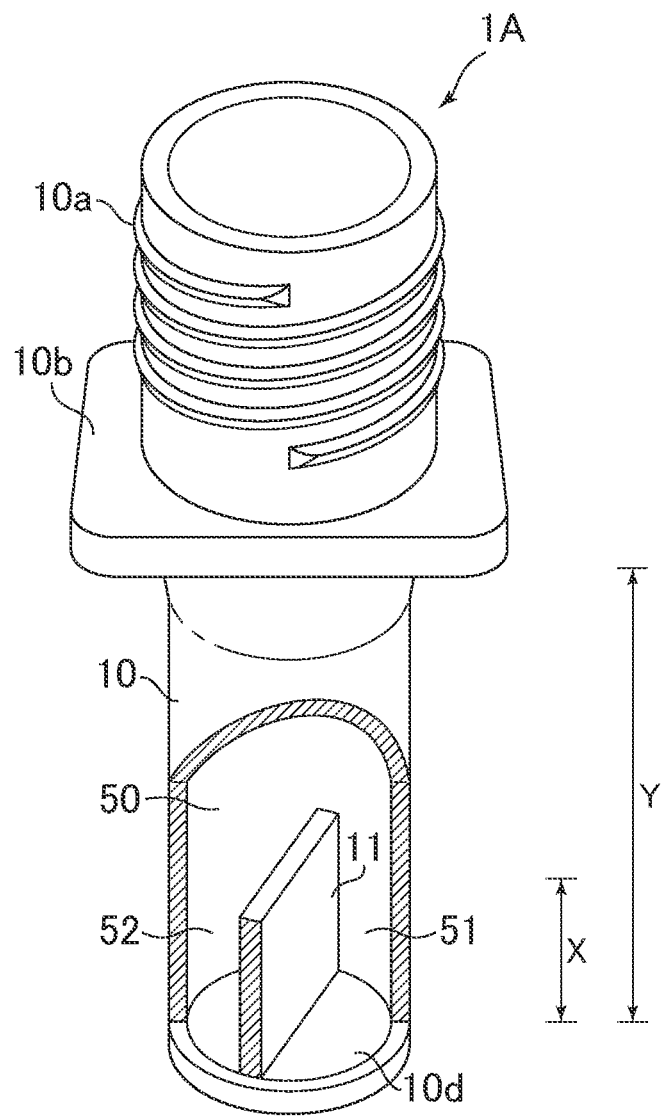
FIG. 1A is a partially cut perspective view of a testing vessel 1A according to an embodiment.

The present invention will now be described with reference to embodiments below. The present invention may also include any other embodiment. The components having the same or similar functions in the figures are denoted by the same or similar reference numerals without redundant description. Since the figures are schematic, the specific size should be determined in view of the following description, for example. It should be noted that the figures have different dimensional relationships or ratios among them.

First Embodiment

[Testing Vessel 1A]

Figure 1B:
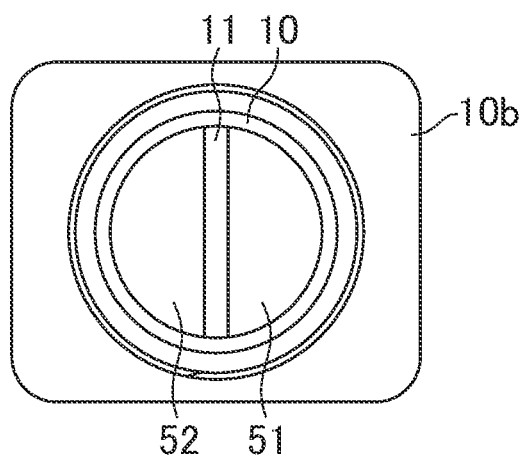
FIG. 1B is a top view of the testing vessel 1A.

FIG. 1A is a partially cut perspective view of a testing vessel according to an embodiment of the present invention, and FIG. 1B is a top view of the testing vessel. As illustrated in FIG. 1A, a testing vessel 1A includes a flexible vessel body 10 having a bottom 10d and a hollow shape; and a vertical partition 11 axially extending from the bottom 10d in the interior of the vessel body 10.

As illustrated in FIG. 1B, the partition 11 divides the bottom face of an analyte extract containable space 50 in the vessel body 10 into a first compartment 51 and a second compartment 52, which allows a first test piece and a second test piece to be immersed in the same analyte extract reserved in the first and second compartments 51 and 52, respectively.

Thus, the testing vessel 1A has advantageous operational effects on a single analyte extract under identical conditions, for example, (1) substantially simultaneous testing for different items with a first test piece and a second test piece and (2) testing for another item with the second test piece after the test with the first test piece as required.

The vessel body 10 may be composed of any material so long as the vessel body 10 can be deformed by external force without impact on the reserved analyte extract during use of the testing vessel and can cause the analyte to be squeezed that is held in a water absorber, such as a pledget, to be immersed in the testing vessel. For example, flexible materials, specifically, resin materials, such as polyethylene, polystyrene, polypropylene, silicone rubber, thermoplastic elastomer, and poly (vinyl chloride), may be used. Their modulus may be adjusted by any well-known process as required.

The vessel body 10 is preferably transparent or semitransparent to facilitate the observation of the internal state of the testing vessel when the analyte is squeezed from, for example, a pledget or when a test piece is immersed.

The vessel body 10 is preferably monolithically molded by any process, for example, by injection molding or 3D printing. An adapter 8 is also produced in a similar manner, which will be described below.

The testing vessel 1A and a testing vessel 1B (described below) each have a bottom and a hollow shape. Alternatively, the testing vessels 1A and 1B may have any size and shape suitable to contain the analyte extract and immerse a swab and preferably have a structure that enables several swabs to be vertically held. Examples of the shape include cylindrical and prismatic, such as quadratic, and hexagonal. The vessel body may have a uniform cross-sectional structure or a partially tapered structure from the top to the bottom.

The testing vessels 1A and 1B each have an opening at one end to enable the analyte extract to be fed. It is also desirable that the opening is provided on the top of the vessel and can be closed by a lid or a seal. For example, as illustrated in FIG. 1A, the opening of the vessel body 10 is preferably provided with a threaded face 10a, which enables the lid to be mounted thereto after filling of the testing vessel with the analyte extract and the lid to be dismounted from the threaded face 10a in use. The test can be thereby facilitated.

The testing vessels 1A and 1B may be further provided with a nonslip structure on the outer wall as required. For example, it is desirable that the testing vessels 1A and 1B each have one or more protrusions and/or recesses. After swabs are immersed into the testing vessels 1A and 1B and then the pledgets of the swabs are rotated and forced to the wall surface of the vessels, a turning force against the testing vessel 1A is generated. The protrusion(s) and/or recess(s) can support swabs to restrain the rotation. An example of such protrusions and/or recesses is an outer rib on the outer wall of the vessel. It is desirable to place the outer rib on the outer wall in the longitudinal direction of the vessel body 10 to restrain the rotation of the testing vessels 1A and 1B and to keep good appearance. As illustrated in FIGS. 1A and 1B, the testing vessels 1A and 1B may be provided with a rib 10b having a substantially square shape in top view in their outer circumference in the boundary between the threaded face 10a and the vessel body 10; this can prevent the testing vessels 1A and 1B from rolling and restrain the slippage when the lid is screwed on or off.

Let the relative height Y of the analyte extract containable space 50 of the vessel body 10 be 2, then the relative height X of the partition 11 is 2 or less, and preferably 1.8 or less, and more preferably 1.7, and more preferably 1.6 to 1.0.

After an analyte is eluted into the analyte extract reserved in the testing vessel 1A, the analyte extract is thoroughly stirred, so that an analyte extract with a uniform analyte concentration is produced. To prevent a difference in concentration between the compartments, the partition may have a communicating hole, so that the analyte extract can be communicated from one compartment to the other.

Any analyte may be analyzed in the testing vessels 1A and 1B. Such analytes include biological samples, such as whole blood, serum, plasma, urine, saliva, induced sputum, nasal discharge, liquid wiped from a nasal cavity or pharynx, sweat, and feces, extracts from foods, such as meat and plants, samples derived from environments, such as waste water, mud flush, and soil, and extracts from microbes and viruses, such as microorganic culture media or suspensions of, for example, microbes and viruses. The analyte may include a variety of target substances, for example, antigens or antibodies in the field of the clinical examination, such as protein antigens derived from viruses, e.g., influenza viruses, RS viruses, adenoviruses, and human metapneumovirus.

When an analyte is supplied to a detection device, the analyte absorbed in, for example, a pledget may be squeezed using a testing vessel and directly supplied to a sample supply site without any process, such as dilution. If the analyte cannot be readily diffused or migrated on a solid phase support due to high viscosity of the analyte, the analyte may be preliminarily diluted with an analyte extract and then be supplied to the detection device.

As long as the target substance can be diffused or spread on the solid phase support for successful detection, the analyte extract may be acidic, neutral, or basic. The analyte extract may contain a buffer solution containing, for example, surfactant and/or modifier and any other solution having any composition.

Any analyte impregnant may be used that can absorb an analyte and desorb it into an analyte extract. Examples of such a material includes a swab and a pledget.

The swab and pledget used for collection of an analyte from a human in the field of clinical assays are often sterilized or disinfected for hygiene. The analyte impregnant may be composed of any other hygienic material having a water absorbency similar to that of the pledget. For example, the analyte impregnant may include any chemical fiber, such as cotton, pulp, or rayon.

[Testing Vessels 2A, 3A, and 4A]

Figure 2A:
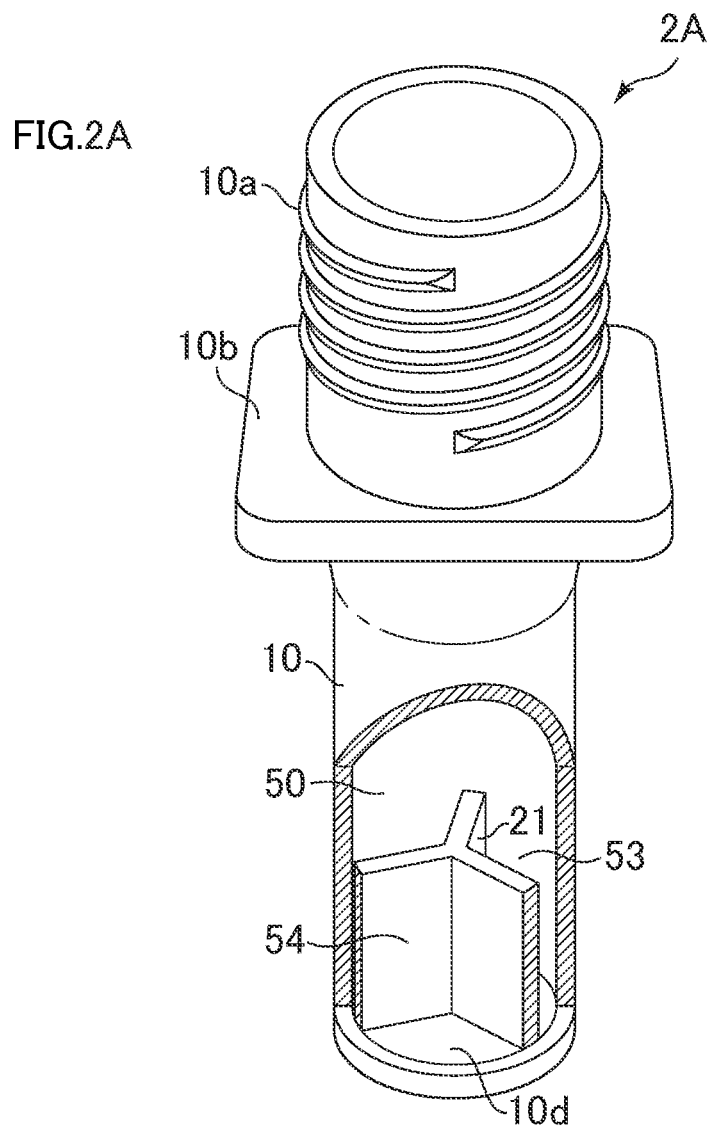
FIG. 2A is a partially cut perspective view of a testing vessel 2A according to an embodiment.
Figure 2B:
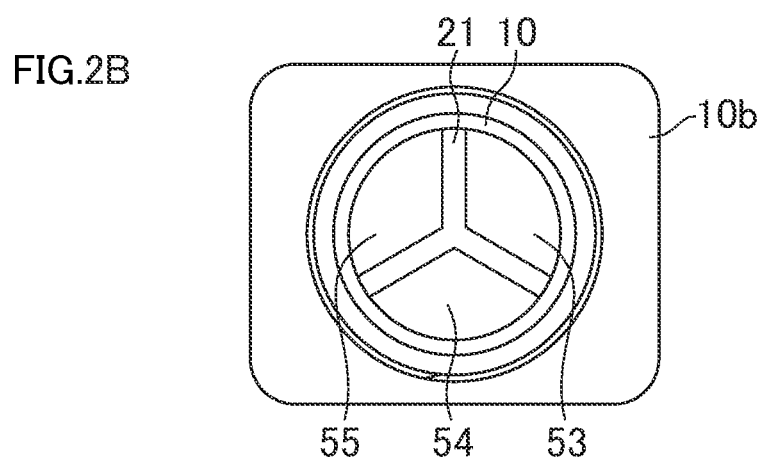
FIG. 2B is a top view of the testing vessel 2A.
Figure 3A:
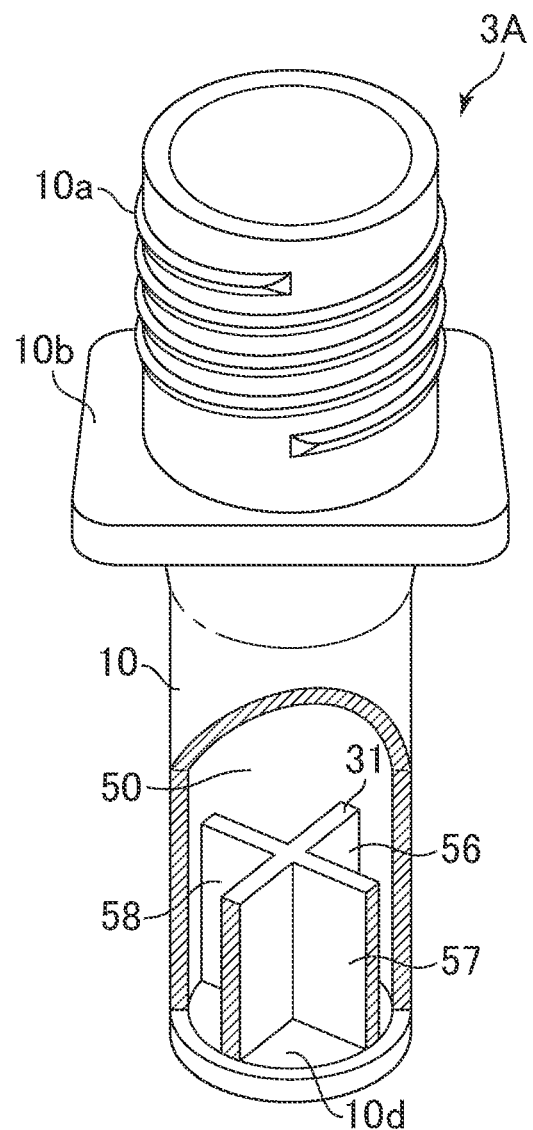
FIG. 3A is a partially cut perspective view of a testing vessel 3A according to an embodiment.
Figure 3B:
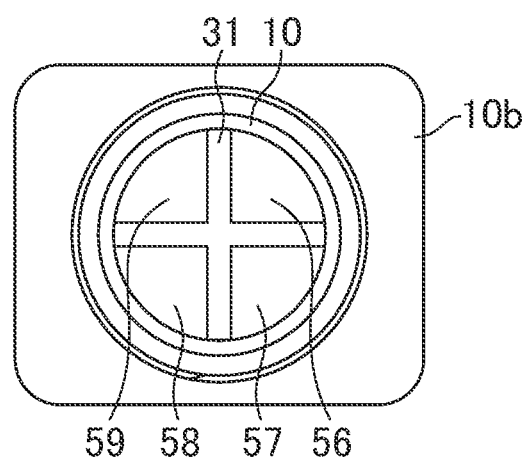
FIG. 3B is a top view of the testing vessel 3A.

An embodiment of the present invention is described with reference to FIGS. 1A and 1B. The invention, however, may include any other embodiment. For example, as illustrated in FIGS. 2A and 2B, a vessel body 10 may include an analyte extract containable space 50 divided into three compartments. This configuration enables, for example, a RS virus, an adenovirus, and a human metapneumovirus to be simultaneously tested in a single analyte extract. As illustrated in FIGS. 3A and 3B, the analyte extract containable space 50 in the vessel body 10 may be divided into four compartments. This configuration enables, for example, tests for four items to be simultaneously performed or tests for three items to be performed followed by an additional test for an item with low sensitivity. The analyte extract containable space 50 may be divided into a larger number of compartments, such as five, six, seven, and more compartments.

Figure 4A:
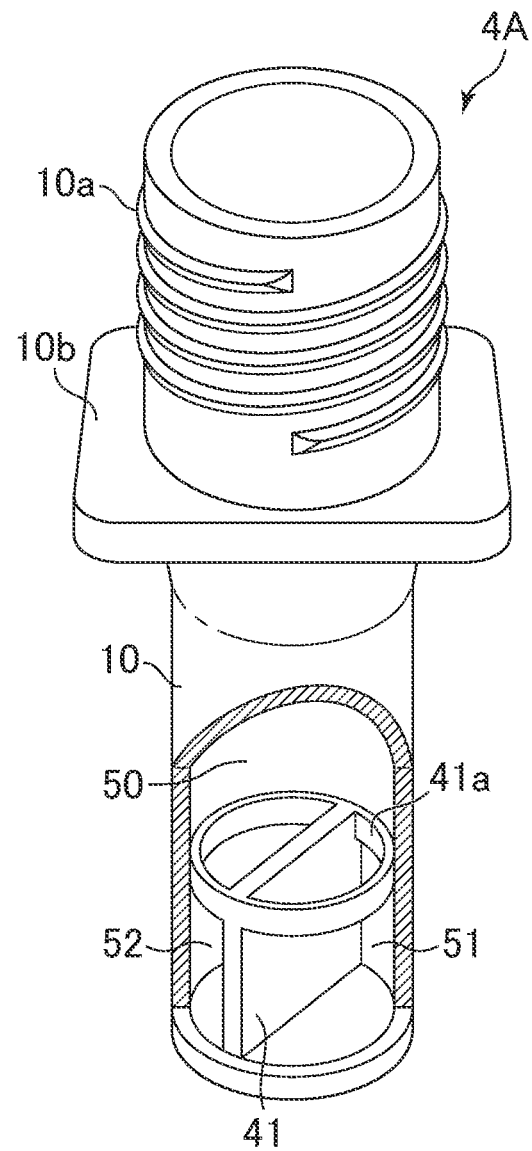
FIG. 4A is a partially cut perspective view of a testing vessel 4A according to an embodiment.
Figure 4B:
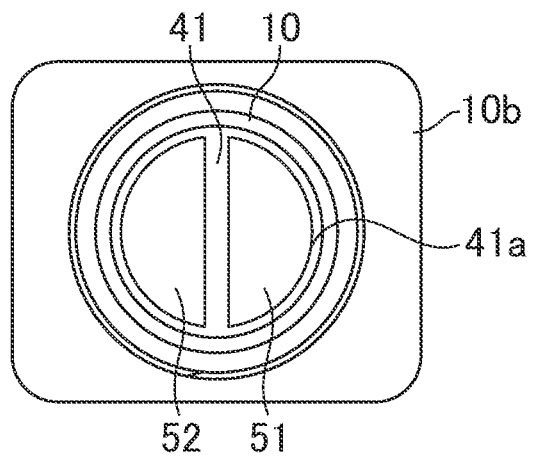
FIG. 4B is a top view of the testing vessel 4A.

As illustrated in FIG. 4A, a partition 41 may be detachably mounted to the interior of the vessel body 10 with a locking member 41a (ring). In FIG. 4A, the locking member 41a is disposed so as to fit to the entire circumference of the vessel body 10. Alternatively, any other geometry may be used. If the partition 41 is fixed in the vessel body 10 and thereby can divide the analyte extract containable space 50 into two or more compartments, the locking member 41a may fit to part of the inner circumference. For example, part of the ring may be omitted into a substantially alphabetic letter "I" or "H" in top view.

[Testing Vessel 5A]

Figure 5A:
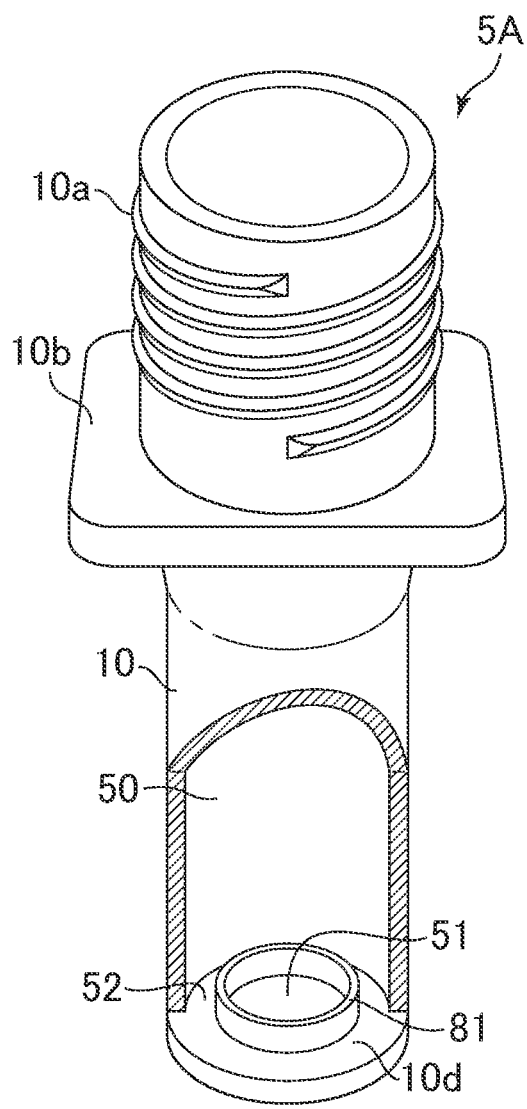
FIG. 5A is a partially cut perspective view of a testing vessel 5A according to an embodiment.
Figure 5B:
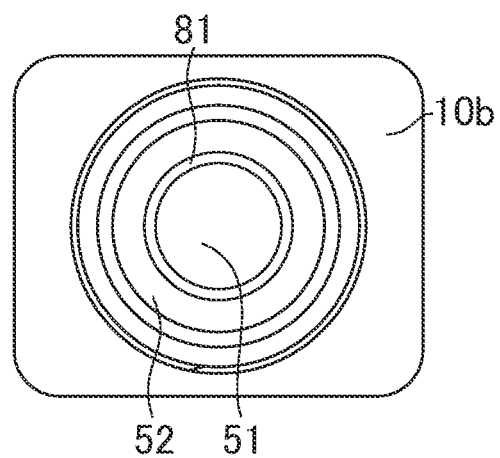
FIG. 5B is a top view of the testing vessel 5A.

The configuration of the testing vessels 1A to 4A including a plate partition is described. Any other configuration may be used if the analyte extract containable space 50 in the vessel body 10 is divided into two or more compartments. For example, as illustrated in FIG. 5A, a hollow cylindrical partition 81 may extend from the bottom 10d of the vessel body 10. The partition 81 illustrated in FIG. 5B has an annular shape in top view. Alternatively, the partition 81 may have a polygonal, e.g., trigonal or tetragonal hollow shape in top view. Alternatively, one or more hollow partitions having a similar shape as the partition 81 may be concentrically disposed in the interior of the partition 81 to divide the analyte extract containable space 50 into two or more compartments. A further partition may be disposed for dividing the space of the partition 81 into two or more compartments and thereby divide the analyte extract containable space 50 into a larger number of compartments. The height of the partition 81 may be the same as that of the testing vessel 1A.

[Testing Method 1A]

The flow of a testing method according to an embodiment will now be described with reference to FIGS. 1A and 6A to 6E.

A flexible testing vessel 1A illustrated in FIG. 1A is prepared. The flexible testing vessel 1A has an internal space axially divided into two compartments. The testing vessel 1A is prefilled with an analyte extract.

As illustrated in FIG. 6A, the lid on the testing vessel 1A is screwed off before use, and then a swab containing an analyte is impregnated with the analyte extract in the testing vessel 1A, as illustrated in FIG. 6B.

As illustrated in FIG. 6C, the swab is clockwise or counterclockwise rotated around its axis. The pledget of the swab may be forced to the inner wall of the vessel.

Subsequently, as illustrated in FIG. 6D, the testing vessel is deformed by external force to rub the pledget against its inner wall such that the analyte is squeezed from the swab.

As illustrated in FIG. 6E, a first test piece 61 is inserted into a first compartment 51 and a second test piece 62 into a second compartment 52 in the testing vessel.

In this manner, the testing method 1A enables the first and second test pieces 61 and 62 to be substantially simultaneously tested for separate items in a single analyte extract under identical conditions.

[Testing method 2A]

Figure 7E:
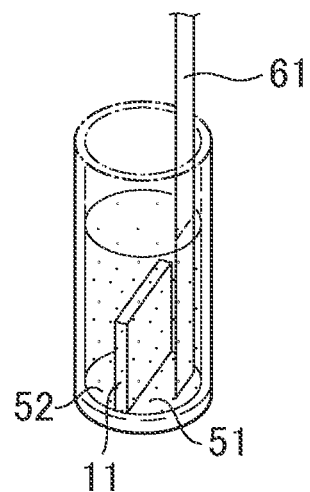
FIGS. 7E to 7G illustrate a process flow of a testing method 2A according to an embodiment.
Figure 7F:
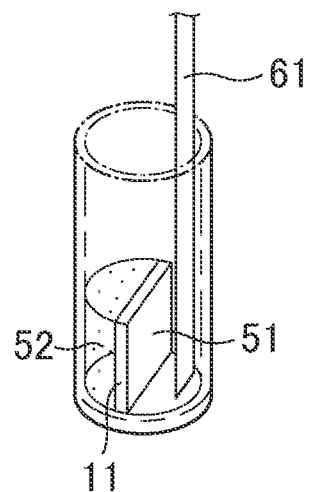
Figure 7G:
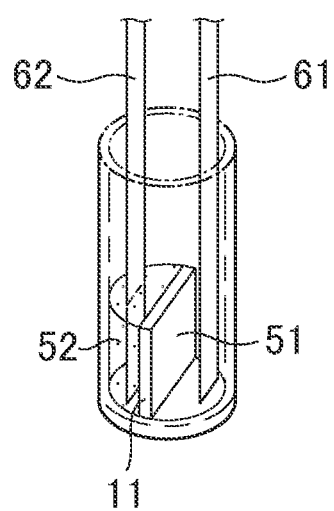

In the testing method 1A, after the steps of FIGS. 6A to 6D, the first test piece 61 and the second test piece 62 are substantially simultaneously immersed in the first compartment 51 and the second compartment 52, respectively, as illustrated in FIG. 6E. Instead of the step of FIG. 6E, as illustrated in FIG. 7E, only the first test piece 61 may be immersed in the first compartment 51. In this manner, even if the first test piece 61 completely absorbs the analyte extract in the first compartment 51 as illustrated in FIG. 7F, the second test piece 62 can be immersed in the second compartment 52 for a test of another item as illustrated in FIG. 7G.

As described above, the testing method 2A enables one or more items with high probability of detection to be initially tested and other items to be tested thereafter depending on the test result(s). The items for the tests can be limited compared with those for the substantially simultaneous test, resulting in highly economic efficiency.

Other Embodiments

As stated above, although the present invention is described with reference to embodiments, it should be understood that the discussions and drawings as part of the present disclosure do not limit the invention. For a person skilled in the art, various alternative embodiments, examples, and operational techniques will be apparent from the disclosure.

Although the description has been focused on the testing vessels 1A to 4A, the present invention also provides, for example, a test kit including any of the testing vessels. The test kit includes a testing vessel containable an analyte extract and a test piece. Two or more test pieces can be included. A single test piece capable of testing two or more items can be used.

The testing methods 1A and 2A have been described. Alternatively, after the steps according to the testing method 2A in FIGS. 7E and 7F, the analyte extract in the second compartment 52 may be fed to any testing device for detection of target substances. For example, various testing methods can be used, such as the dipstick test guiding a test piece in a testing vessel for immersion in an extract, the lateral flow test supplying an extract to a testing device, and the flow-through test.

It should be appreciated that the present invention includes various embodiments that are not described herein. The technical scope of the present invention is thus defined solely by the matter(s) specifying the invention according to Claims resulted from the description above.

EXAMPLE 1A

Polyethylene was used for a molding material. A testing vessel 1A illustrated in FIGS. 1A and 1B was prepared by injection molding. Subsequently, an experiment was performed according to the procedures of the testing method 1A. Positive analytes for a RS virus, an adenovirus, and a rotavirus, respectively, were used as analytes. A test piece of Rapid Tester (registered trademark) RSV-adeno (available from Sekisui Medical) was used for a first test piece, and that of Rapid Tester (registered trademark) Rota-Adeno (available from Sekisui Medical) was used for a second test piece. Both the first and second test pieces exhibited good test results.

COMPARATIVE EXAMPLE 1A

A testing vessel with the same configuration as those in FIGS. 1A and 1B except for the absence of the partition 11 was prepared, and the same experiment as that of Example 1A was performed. The first test piece interfered with the second test piece, resulting in insufficient absorption of the second test piece.

EXAMPLE 2A

Polyethylene was used for a molding material. A testing vessel 1A illustrated in FIGS. 1A and 1B was prepared by injection molding. Subsequently, an experiment was performed according to the procedure of the testing method 2A. Positive analytes for a RS virus, an adenovirus, and rotavirus, respectively, were used as analytes. A test piece of Rapid Tester (registered trademark) RSV-Adeno (available from Sekisui Medical) was used for a first test piece, and that of Rapid Tester (registered trademark) Rota-Adeno (available from Sekisui Medical) was used for a second test piece. Both the first and second test pieces exhibited good test results.

COMPARATIVE EXAMPLE 2A

A testing vessel with the same configuration as those in FIGS. 1A and 1B except for the absence of the partition 11 was prepared, and the same experiment as that of Example 2A was performed. The first test piece completely absorbed the analyte extract, and thus the test for another item with the second test piece could not be performed.

Second Embodiment

A second embodiment will be described, focusing on the difference from the first embodiment.

[Testing Vessel 1B]

Figure 8A:
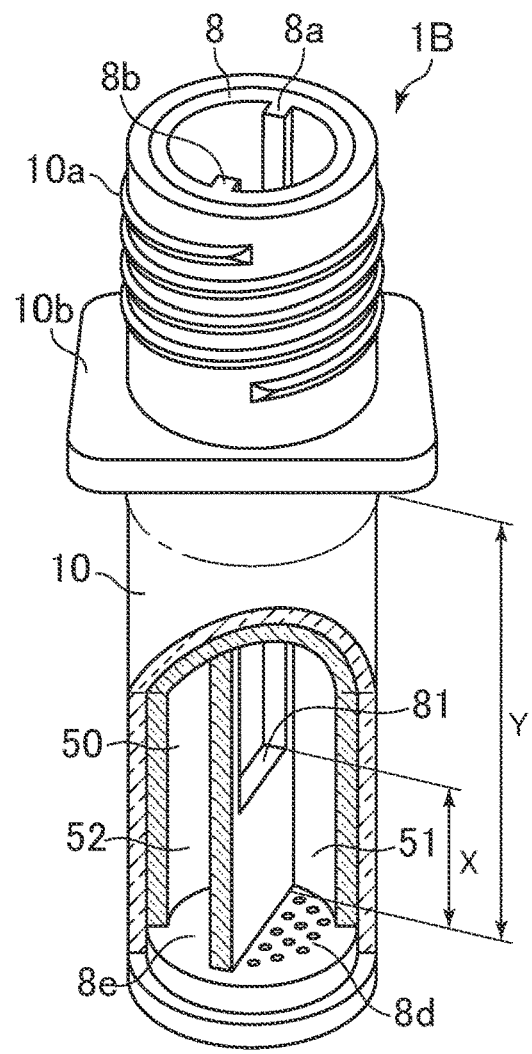
FIG. 8A is a partially cut perspective view of the testing vessel 1B according to an embodiment.
Figure 8B:
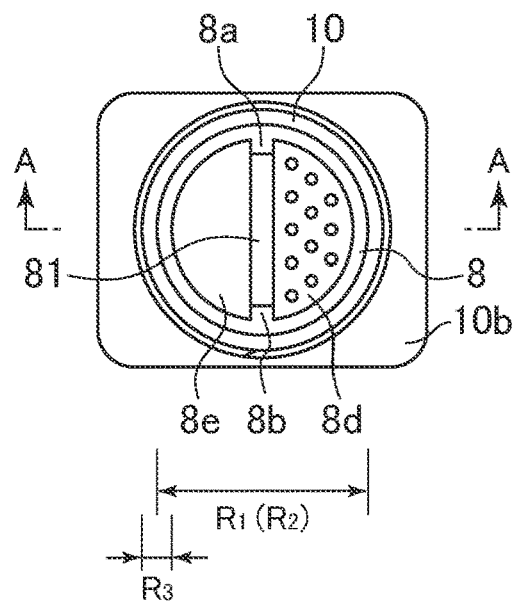
FIG. 8B is a top view of the testing vessel 1B.
Figure 9A:
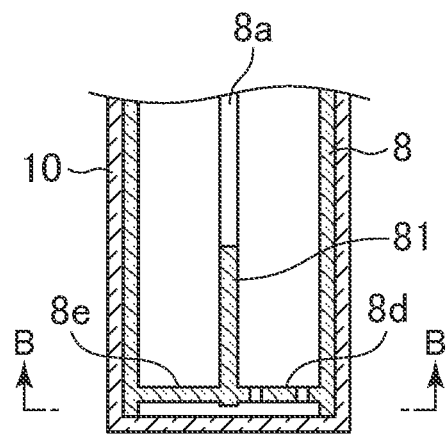
FIG. 9A is a cross-sectional view taken from line A-A of the testing vessel 1B according to an embodiment.
Figure 9B:
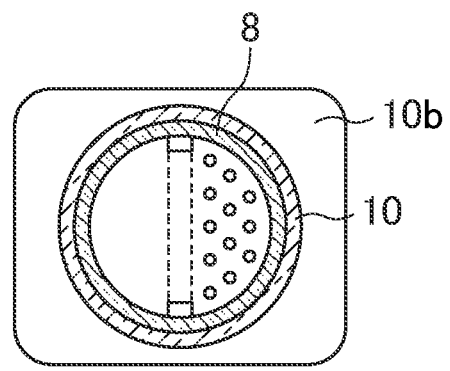
FIG. 9B is a cross-sectional view taken from line B-B of the testing vessel 1B.

FIG. 8A is a partially cut perspective view of a testing vessel according to an embodiment of the present invention, and FIG. 8B is a top view thereof. As illustrated in FIG. 8A, the testing vessel 1B includes a flexible vessel body 10 having bottom and a hollow shape; and an adapter 8 having a bottom segments 8d and 8e and a hollow shape and being detachably mounted to the interior of the vessel body 10. The adapter 8 includes a partition 81 extending from the bottom segments 8d and 8e (a first face) of the adapter 8 to an opening and dividing an analyte extract containable space 50 of the adapter into two or more compartments.

As illustrated in FIG. 8A, the partition 81 divides the bottom face of the analyte extract containable space 50 in the vessel body 10 into a first compartment 51 and a second compartment 52, which allows the first test piece and the second test piece to be immersed in a single analyte extract reserved in the first compartment 51 and the second compartment 52, respectively.

Thus, the testing vessel 1B has advantageous operational effects on a single analyte extract under identical conditions, for example, (1) substantially simultaneous testing for different items with a first test piece and a second test piece and (2) testing for another item with the second test piece after the test with the first test piece as required.

As illustrated in FIG. 8A, the adapter 8 preferably has guides 8a and 8b extending from the boundary of the compartments in the adapter 8 to the opening of the adapter 8 because the boundary can be readily visually observed when a test piece is immersed in the vessel. The guides locking the test pieces also prevents one of the test pieces from falling into the compartment of the other.

To facilitate the visual observation of the boundary of the compartments, for example, the guides 8a and 8b may be shaped such that the upper end of the guides 8a and 8b is located above the edge of the opening of the vessel body 10 when the adapter 8 is fixed to the interior of the vessel body 10. Alternatively, a collar may be provided that protrudes from the upper end of the opening at the guides 8a and 8b to the exterior of the vessel body.

As illustrated in FIG. 8B, the adapter 8 preferably has one or more through holes or preferably slots defined in any of the bottom segments of two or more compartments. This facilitates the analyte extract in the vessel body to move into adapter 8 via the through holes when the adapter 8 is inserted into the vessel body reserving the analyte extract as illustrated in FIG. 14E, which will be described below.

To perform a testing method 2B to be described below, at least one of the compartments preferably has no through hole in the bottom segment to prevent the flow of the analyte extract from the second compartment 52 to the first compartment 51.

Any material may be used for the adapter 8 as long as the material does not affect on the reserved analyte extract. For example, flexible materials, specifically resin materials, such as polyethylene, polystyrene, polypropylene, silicone rubber, thermoplastic elastomer, and poly (vinyl chloride), can be used.

Let the height Y of the analyte extract containable space 50 in the vessel body 10 be 2, the height X of the partition 81 in the adapter is 2 or less, preferably 1.8 or less, more preferably 1.7 or less, and more preferably 1.2 to 0.5.

After an analyte is eluted into the analyte extract reserved in the testing vessel 1B, the analyte extract is thoroughly stirred, so that an analyte extract with a uniform analyte concentration is produced. To prevent a difference in concentration between the compartments after the adapter 8 is inserted into the vessel body 10, the partition 81 in the adapter may have a communicating hole, so that the analyte extract can be communicated from one compartment to the other.

[Modification of the Testing Vessel 1B]

Figure 10A:
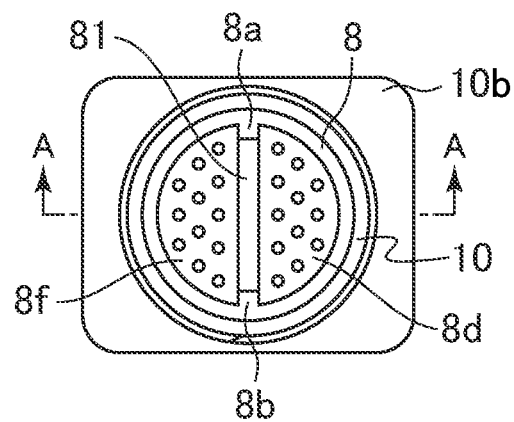
FIG. 10A is a top view of a modification of the testing vessel 1B according to an embodiment.
Figure 10B:
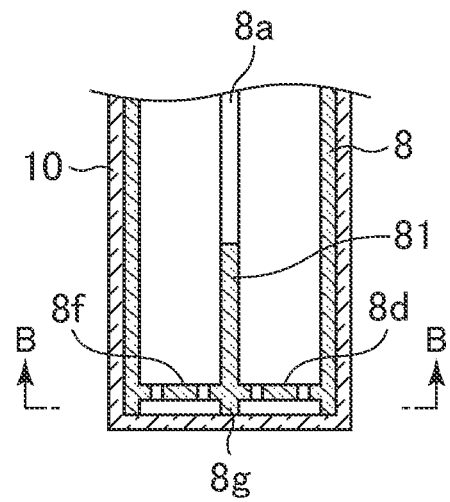
FIG. 10B is a cross-sectional view taken from line A-A of the modification of the testing vessel 1B.
Figure 10C:
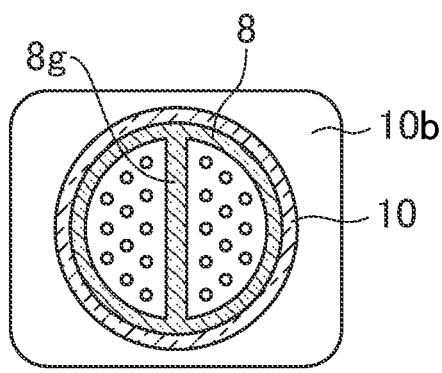
FIG. 10C is a cross-sectional view taken from line B-B of the modification of the testing vessel 1B.

Although the present invention is described with reference to FIGS. 8A, BB, 9A, and 9B, the present invention may include any other invention. FIG. 10A is a top view of a modification of the testing vessel 1 according to an embodiment. FIG. 10B is a cross-sectional view taken from line A-A. FIG. 10C is a cross-sectional view taken from line B-B.

The testing vessel in FIG. 8A does not have a through hole formed in the bottom segments of the second compartment 52 to prevent the flow of the analyte extract from the second compartment 52 to the first compartment 51. Alternatively, any other configuration may be used for preventing the flow of the analyte extract. For example, as illustrated in FIG. 10B, the adapter 8 having a raised bottom may include a baffle plate 8g disposed along the boundary between the bottom segment 8d and the bottom segment 8f of the compartments on the lower face (a second face) of the adapter 8 so as to be in contact with the upper face (a third face) of the vessel body 10. The baffle plate 8g blocks the flow of the analyte extract between the compartments.

The adapter 8 has a through hole in the bottom. Alternatively, the through hole may be disposed anywhere else on the adapter 8, for example, in the side wall.

The adapter 8 has a bottom and a hollow shape. Alternatively, the adapter 8 does not need the bottoms if the adapter 8 internally includes a partition that can be held by the sidewall.

[Testing Vessels 2B and 3B]

Figure 11A:
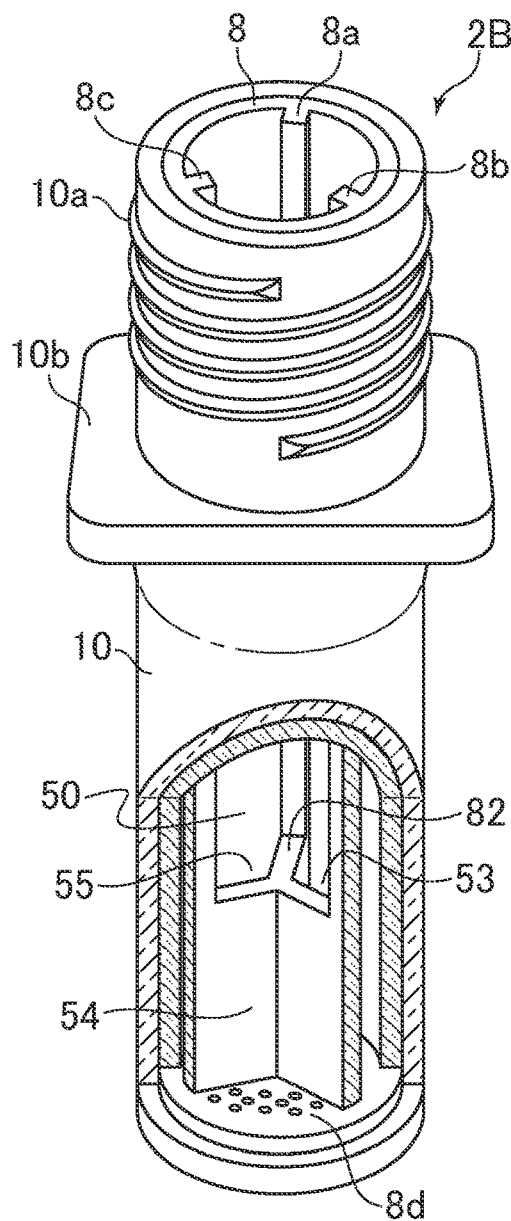
FIG. 11A is a partially cut perspective view of a testing vessel 2B according to an embodiment.
Figure 11B:
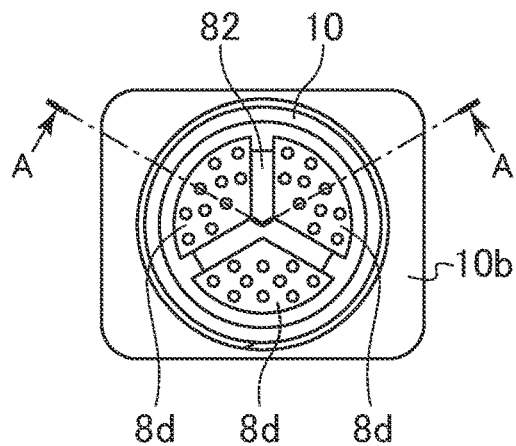
FIG. 11B is a top view of the testing vessel 2B.
Figure 11C:
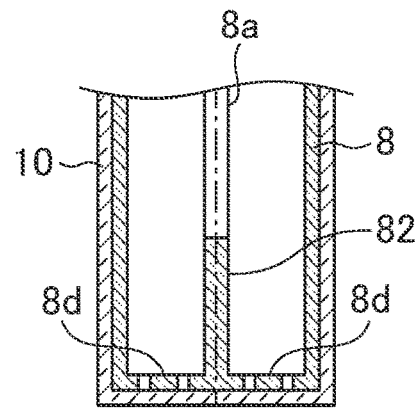
FIG. 11C is a cross-sectional view taken from line A-A of the testing vessel 2B.

As illustrated in FIGS. 11A and 11B, the analyte extract containable space 50 in the vessel body 10 may be divided into three compartments. This enables, for example, a RS virus, an adenovirus, and a human metapneumovirus to be simultaneously tested in a single analyte extract. To perform the testing method 2B to be described below, as illustrated in FIG. 11C, the bottom of the adapter 8 may be adapted to be inclose contact with the bottom of the vessel body 10 to block the inflow of the analyte extract.

Figure 12A:
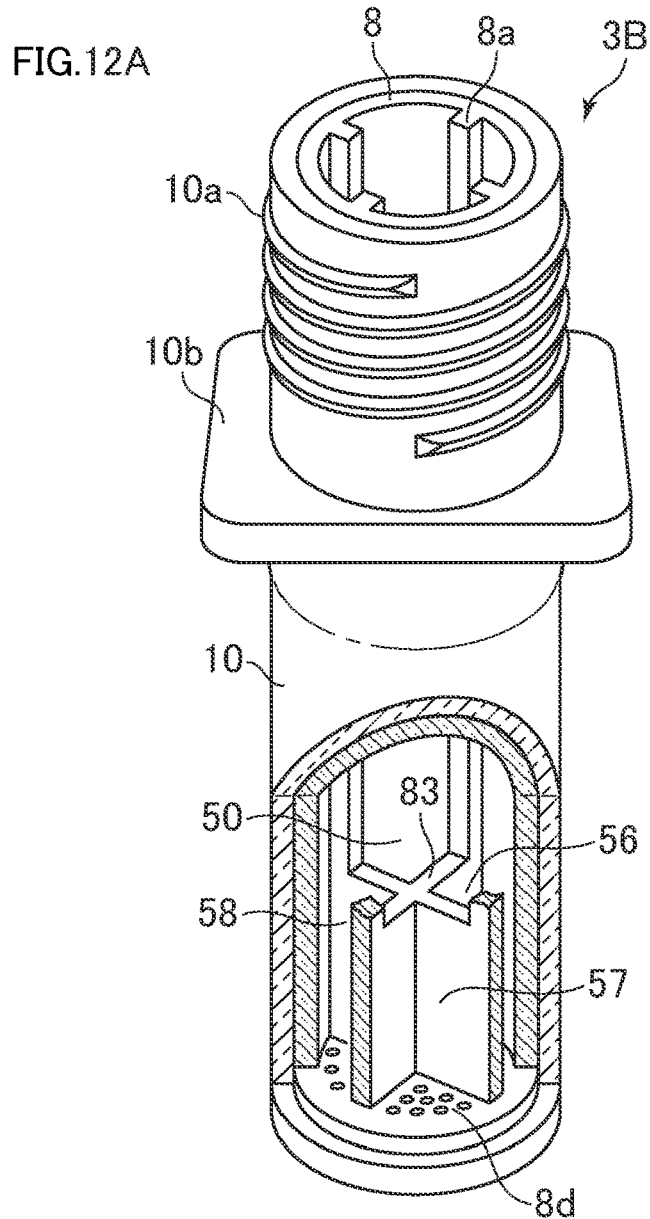
FIG. 12A is a partially cut perspective view of a testing vessel 3B according to an embodiment.
Figure 12B:
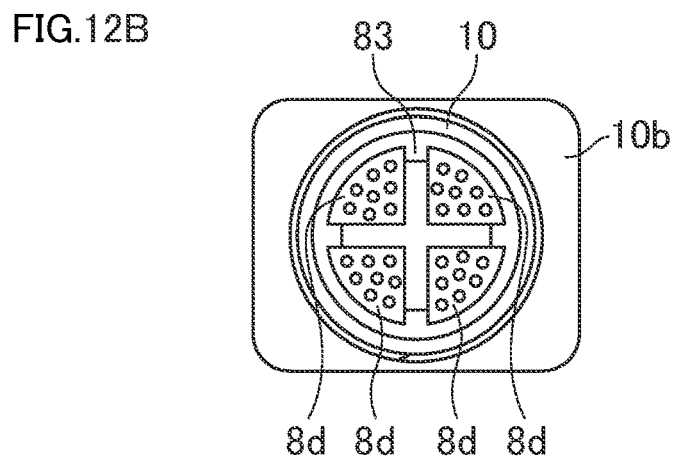
FIG. 12B is a top view of the testing vessel 3B.

As illustrated in FIGS. 12A and 12B, the analyte extract containable space 50 in the vessel body 10 may be divided into four compartments. This enables, for example, tests for four items to be simultaneously performed or test for three items to be performed followed by an additional test for an item with low sensitivity. The analyte extract containable space 50 may be divided into a larger number of compartments, such as five, six, seven, and more compartments.

[Testing Vessel 4B]

Figure 13A:
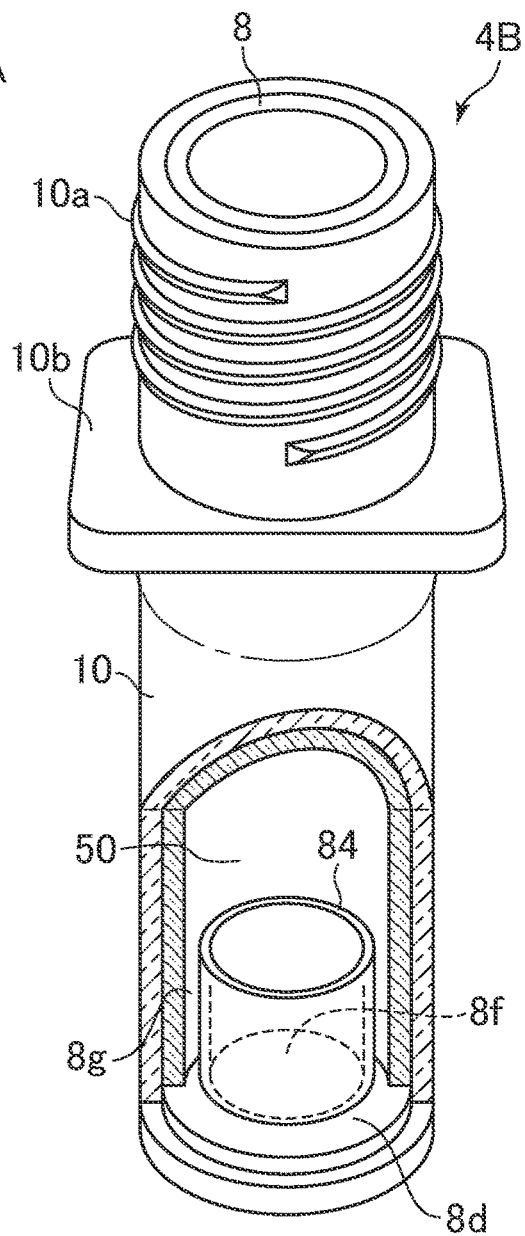
FIG. 13A is a partially cut perspective view of a testing vessel 4B according to an embodiment.
Figure 13B:
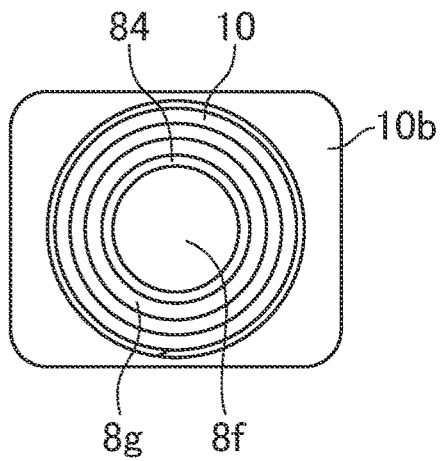
FIG. 13B is a top view of the testing vessel 4B.

The testing vessels 1B to 3B each include a plate partition. Alternatively, any other type of partition may be used as long as the analyte extract containable space 50 can be divided into two or more compartments. For example, as illustrated in FIG. 13A, a partition 84 may have a hollow cylindrical shape extending from the bottom segment 8d in the adapter 8. The partition 84 has a cylindrical shape in top view as illustrated in FIG. 13B. Alternatively, the partition 84 may have a polygonal, e.g., trigonal or tetragonal hollow shape in top view. Alternatively, one or more hollow partitions having a similar shape as the partition 84 may be concentrically disposed in the interior of the partition 84 to divide the analyte extract containable space 50 into two or more compartment. A further partition may be disposed for dividing the space of the partition 84 in two or more compartments and thereby divide the analyte extract containable space 50 into a larger number of compartments. The height of the partition 84 may be the same as that of the testing vessel 1A.

[Testing Method 1B]

The flow of a testing method according to an embodiment will now be described with reference to FIGS. 8A and 14A to 14F1.

A flexible vessel body 10 is prepared having a bottom and a hollow shape as illustrated in FIG. 8A. The flexible vessel body 10 is prefilled with an analyte extract.

Figure 14A:
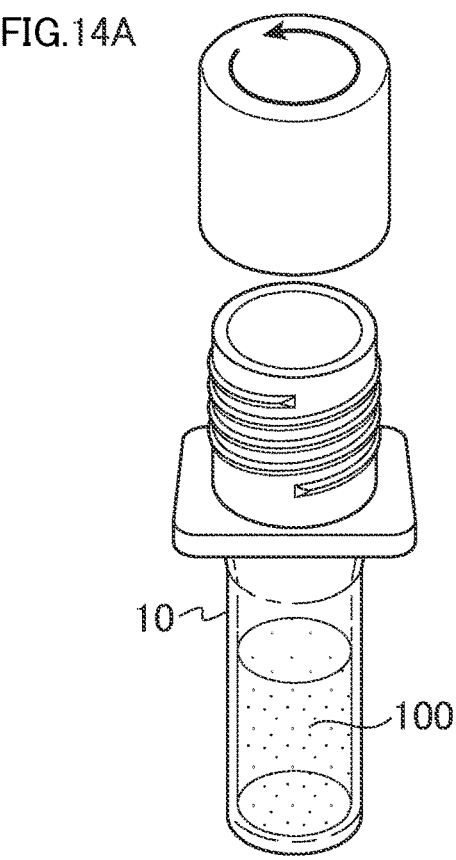
Figure 14B:
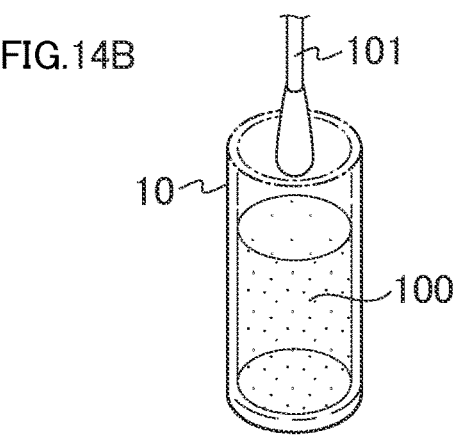

As illustrated in FIG. 14A, the lid on the vessel body 10 is screwed off before use, and then a swab 101 containing an analyte is impregnated with an analyte extract 100 in the vessel body 10, as illustrated in FIG. 14B.

Figure 14C:
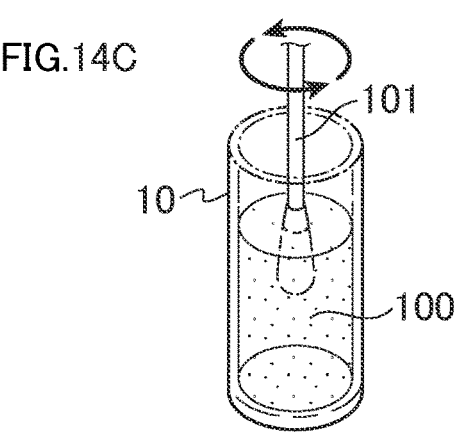

As illustrated in FIG. 14C, the swab 101 is clockwise or counterclockwise rotated around its axis. The pledget of the swab 101 may be forced to the inner wall of the vessel.

Figure 14D:
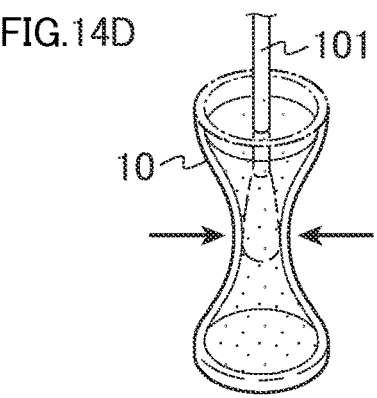
Figure 14E:
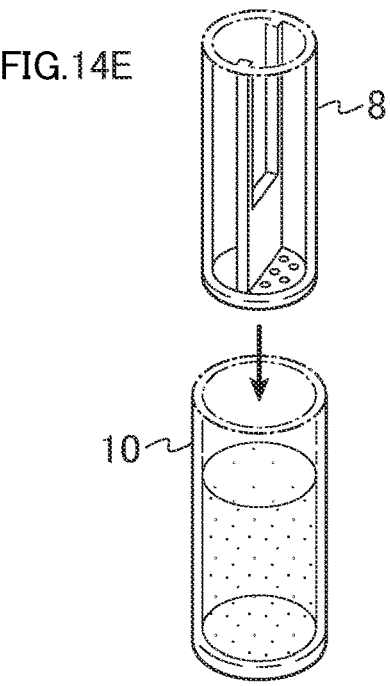
Figure 14E:
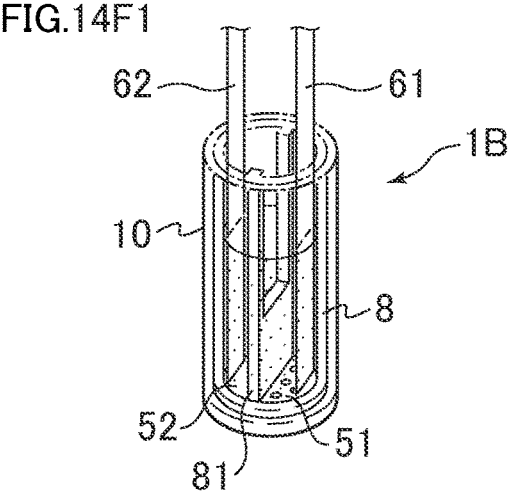
Figure 16:
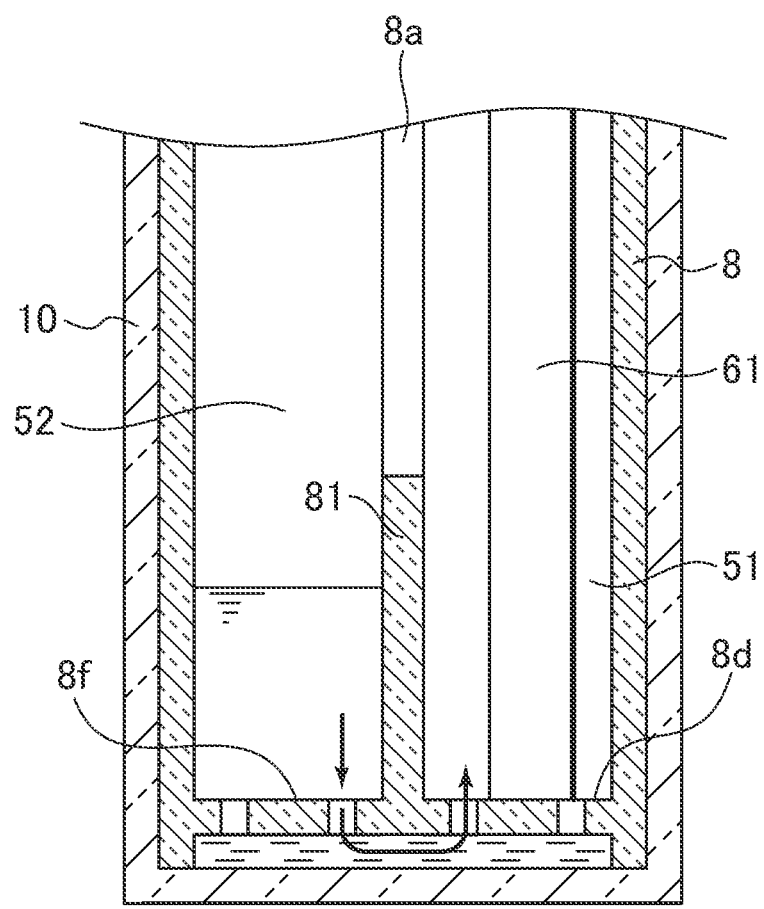
FIG. 16 is a process flow view of a testing method B.

Subsequently, as illustrated in FIG. 14D, the vessel body 10 is deformed by external force to rub the pledget against its inner wall such that the analyte is squeezed from the swab 101.

As illustrated in FIG. 14E, an adapter 8 is inserted into the vessel body 10. The adapter 8 is preferably inserted slowly such that the analyte extract moves into the adapter 8 via the through hole in the bottom of the adapter 8.

As illustrated in FIG. 14F1, a first test piece 61 is inserted into a first compartment 51 of the testing vessel 1B and a second test piece 62 into a second compartment 52 of the testing vessel 1B.

In this manner, the testing method 1B enables the first and second test pieces 61 and 62 to be substantially simultaneously tested for separate items in a single analyte extract under identical conditions.

In the testing method 1B, the adapter 8 is inserted after squeezing of an analyte. In the step of squeezing the analyte from a swab in FIG. 14D, the absence of a partition enables the analyte to be more effectively squeezed. When the adapter 8 is inserted into the vessel body 10, an analyte suspension on the wall surface of the vessel body 10 can be collected from the wall surface, resulting in an advantageous effect that a sufficient analyte volume or liquid volume necessary for measurement in the first compartment 51 and the second compartment 52 can be secured.

Thus, a partition is more preferably disposed on the bottom of the adapter 8 detachably mounted to the interior of the vessel body 10.

To collect an analyte suspension on the wall surface, the outer circumference of the adapter 8 is preferably in close contact with the inner circumference of the vessel body 10. Specifically, the outer radius of the adapter 8 is preferably larger than the inner radius of the vessel body 10. Even if the outer radius of the adapter 8 is slightly larger than the inner radius of the vessel body 10, use of a flexible material for the vessel body 10 enables the adapter 8 to be guided into the vessel body 10 such that the outer circumference of the adapter 8 is in close contact with the inner circumference of the vessel body 10. The outer radius of the adapter 8 is preferably equal to or larger than the inner radius of the vessel body 10.

[Testing Method 2B]

In the testing method 1B, after the steps of FIGS. 14A to 14E, the first test piece 61 and the second test piece 62 are substantially simultaneously inserted into the first compartment 51 and the second compartment 52, respectively, as illustrated in FIG. 14F1. Instead of the steps of FIG. 14F1, as illustrated in FIG. 15F2, only the first test piece 61 may be inserted into the first compartment 51. Even if the first test piece 61 completely absorbs the analyte extract in the first compartment 51 as illustrated in FIG. 15G, the second test piece 62 can be subsequently inserted into the second compartment 52 for a test of another item as illustrated in FIG. 15H.

In this manner, the testing method 2B enables an item with high probability of detection to be initially tested and another item to be tested thereafter depending on the test result as required. The items for the tests can be limited compared with those for the simultaneous test, resulting in highly economic efficiency.

For performance of the testing method 2B, no through hole is preferably provided in the bottom segment He of the second compartment 52 to block the flow of the analyte extract from the second compartment 52 to the first compartment 51 as illustrated in FIGS. 8A and 8B.

If through holes are provided across the raised bottom, a baffle plate 8g is preferably provided as illustrated in FIG. 10B. In addition, as illustrated in FIG. 11C, the bottom of the adapter 8 is provided to be in close contact with the bottom of the vessel body.

Other Embodiments

As described above, the present invention is described with reference to embodiments. It should not be appreciated, however, that the discussions and drawings limit the invention. For a person skilled in the art, various alternative embodiments, examples, and operational techniques will be apparent from the disclosure.

Although the description has been focused on the testing vessels 1B to 4B, the present invention also provides, for example, a test kit including any of the testing vessels. The test kit includes a testing vessel containable an analyte extract and a test piece. Two or more test piece can be included. A single test piece capable of testing two or more items can be used.

The testing methods 1B and 2B have been described. Alternatively, after the steps according to the testing method 2B in FIGS. 15F2 and 15G, the analyte extract in the second compartment 52 may be fed to any testing device for detection of target substances. For example, various testing methods can be used, such as the dipstick test guiding a test piece in a testing vessel for immersion in an extract, the lateral flow test supplying an extract to a testing device, and the flow-through test.

It should be appreciated that the present invention includes various embodiments that are not described herein.

The technical scope of the present invention is thus defined solely by the matter(s) specifying the invention according to Claims resulted from the description above.

EXAMPLE 1B

Polyethylene was used for a molding material. A testing vessel 1B illustrated in FIGS. 8A and 8B was prepared by injection molding. Subsequently, an experiment was performed according to the procedures of the testing method 1B. Positive analytes for a RS virus, an adenovirus, and a rotavirus, respectively, were used as analytes. A test piece of Rapid Tester (registered trademark) RSV-adeno (available from Sekisui Medical) was used for a first test piece, and that of Rapid Tester (registered trademark) Rota-Adeno (available from Sekisui Medical) was used for a second test piece. Both the first and second test pieces exhibited good test results.

COMPARATIVE EXAMPLE 1B

A testing vessel with the same configuration as those in FIGS. 8A and 8B except for the absence of the partition 11 was prepared, and the same experiment as that of Example 1B was performed. The first test piece interfered with the second test piece, resulting in insufficient absorption of the second test piece.

EXAMPLE 2B

Polyethylene was used for a molding material. A testing vessel 1B illustrated in FIGS. 8A and 8B was prepared by injection molding. Subsequently, an experiment was performed according to the procedure of the testing method 2B. Positive analytes for a RS virus, an adenovirus, and rotavirus, respectively, were used as analytes. A test piece of Rapid Tester (registered trademark) RSV-Adeno (available from Sekisui Medical) was used for a first test piece, and that of Rapid Tester (registered trademark) Rota-Adeno (available from Sekisui Medical) was used for a second test piece. Both the first and second test pieces exhibited good test results.

COMPARATIVE EXAMPLE 2B

The testing vessel with the same configuration as those in FIGS. 8A and 8B except for the absence of the partition 11 was prepared, and the same experiment as that of Example 2B was performed. The first test piece completely absorbed the analyte extract, and thus the test for another item with the second test piece could not be performed.

REFERENCE SIGNS LIST 1A, 2A, 3A, 4A, 5A, 1B, 2B, 3B, and 45 testing vessel
8 adapter
8a and 8b guides
10 vessel body
11, 21, 31, 41, 81, 82, 83, and 84 partition
50 analyte extract containable space
51 first compartment
52 second compartment
61 and 62 test pieces

The invention claimed is:
1. A testing vessel comprising:
  a flexible vessel body having a bottom and a hollow shape; and
  an adapter detachably mounted to an interior of the vessel body, the adapter having a bottom and a hollow shape;
  wherein the adapter comprises a partition extending from the bottom of the adapter toward an opening of the adapter, the partition dividing an analyte extract containable space in the adapter into two or more compartments,
  a ratio of height X of the partition in the adapter to height Y of the analyte extract containable space in the vessel body (X:Y) is 0.5:2 to 1.2:2, and
  the adapter further comprises guides each extending along an inner wall of the adapter from an upper boundary of the compartments to the opening, and having a convex shape extruding from the inner wall toward a center axis of the adapter.
2. The testing vessel according to claim 1, wherein the adapter has a through hole defined in a portion thereof.
3. The testing vessel according to claim 1, wherein the adapter has a through hole in at least one of bottom segments of the compartments.
4. The testing vessel according to claim 1, wherein the guides of the adapter each have an upper end located above an upper edge of an opening of the vessel body.
5. The testing vessel according to claim 4, wherein the guides each comprise a collar protruding from the upper end of the guide at the opening of the adapter to an exterior of the testing vessel.
6. The testing vessel according to claim 1, wherein the adapter comprises a baffle plate disposed along the boundary between the bottom segments of the compartments on a lower face of the adapter so as to be in contact with an upper face of the vessel body, the baffle plate blocking the flow of a solution between the compartments.
7. The testing vessel according to claim 1, wherein the adapter body has the analyte extract containable space divided into three or more compartments.
8. The testing vessel according to claim 1, wherein an outer radius of the adapter is equal or larger than an inner radius of the vessel body.
9. A test kit comprising:
  the testing vessel according to claim 1;
  an analyte extract contained in the testing vessel; and
  a test piece.
10. A testing method comprising:
  impregnating a swab containing an analyte with an analyte extract in a flexible vessel body, the vessel body having a bottom and a hollow shape;
  squeezing the analyte from the swab by deforming the testing vessel with external force;
  inserting an adapter into the vessel body, the adapter having a bottom and a hollow shape, the adapter comprising a partition for dividing an analyte extract containable space in the adapter into two or more compartments, the partition extending from the bottom of the adapter toward an opening of the adapter, at least one of the compartments having a through hole defined in the bottom, and the adapter further comprising guides each extending along an inner wall of the adapter from an upper boundary of the compartments to the opening, and having a convex shape extruding from the inner wall toward a center axis of the adapter; and
  immersing a first test piece into a first compartment of the compartments, wherein a ratio of height X of the partition in the adapter to height Y of the analyte extract containable space in the vessel body (X:Y) is 0.5:2 to 1.2:2.

11. The testing method according to claim 10, further comprising immersing a second test piece into a second compartment of the compartments.

12. The testing method according to claim 11, wherein the second test piece is immersed substantially simultaneously with or after immersing the first test piece.

* * * * *